United States Patent [19]
Witter

[11] Patent Number: 5,849,299
[45] Date of Patent: *Dec. 15, 1998

[54] ATTENUATED REVERTANT SEROTYPE 1 MAREK'S DISEASE VACCINE

[75] Inventor: Richard L. Witter, Okemos, Mich.

[73] Assignee: The United States of America as represented by the Secretary of Agriculture, Washington, D.C.

[*] Notice: The portion of the term of this patent subsequent to Jan. 23, 2007, has been disclaimed.

[21] Appl. No.: 723,037

[22] Filed: Jun. 28, 1991

[51] Int. Cl.$^6$ .................................................. A61K 39/255
[52] U.S. Cl. .................. 424/229.1; 435/691; 435/235.1; 435/237; 435/239; 435/238
[58] Field of Search .................................. 424/89, 229.1; 435/235.1, 69.1, 237, 238, 239

[56] References Cited

U.S. PATENT DOCUMENTS

| | | | |
|---|---|---|---|
| 4,673,572 | 6/1987 | de Boer | 424/89 |
| 4,895,717 | 1/1990 | Witter . | |

OTHER PUBLICATIONS

R. L. Witter, "Protection by Attenuated and Polyvalent Vaccines Against Highly Virulent Strains of Marek's Disease Virus," Avian Pathol. 11:49–62 (1982).

R. L. Witter et al., "Polyvalent Marek's Disease Vaccines: Safety, Efficacy and Protective Synergism in Chickens with Maternal Antibodies" Avian Pathol. 13: 75–92 (1984).

R. L. Witter, "Attenuated Revertant Serotype 1 Marek's Disease Viruses: Safety and Protective Efficacy" Avian Diseases 35: 877–891 (1991).

Witter, R.L. (87a) Avian Dis. 31:752–765.

Witter, R.L. (87b) Avian Dis. 31:829–840.

Hirai, K. et al. (81) Virology 115:385–389.

Iakovleva, L.S. et al (77) Vopr. Virusol. 4:493–497 (abstract only).

Churchill, A.E. et al. (69) J. Gen. Virol. 4:557–564.

Sharma, J.M. et al. (82) Avian Dis. 26:860–870.

Finkelstein, A. et al. (1989) Trends in Biotechnology 7:273–277.

de Boer, G.F. et al (1987) Vet Q. 9 Suppl. 1 165–285 (abstract only).

*Primary Examiner*—Anthony C. Caputa
*Attorney, Agent, or Firm*—Curtis P. Ribando; M. Howard Silverstein; John D. Fado

[57] ABSTRACT

A Marek's disease vaccine comprising an attenuated revertant virus derived as a clone of Md11/75/R2 or an antigenic component of the virus is characterized by a markedly reduced pathogenicity compared to the parent virus, without a comparable loss in immunogenicity. Attenuated revertants of the invention are exemplified by Md11/75/R2/23 and Md11/75/R2/29. These viruses or immunogenic components thereof can be formulated into monovalent and polyvalent vaccines.

6 Claims, No Drawings

ATTENUATED REVERTANT SEROTYPE 1 MAREK'S DISEASE VACCINE

BACKGROUND OF THE INVENTION

1. Field of the Invention

Marek's disease (MD), a highly prevalent and important lymphoproliferative disease of chickens, is controlled in commercial chickens by live virus vaccines consisting of attenuated or naturally avirulent MD-related herpesviruses. Although vaccination programs have been considered highly effective overall, the poultry industry continues to experience losses due to MD. Given the tendency of MD virus to became more virulent with time coupled with the economic pressures confronting the poultry industry, there is still a strong incentive to develop even more efficacious products that will protect better in the face of early challenge with very virulent field strains. This invention relates to a novel vaccine against MD which does in fact provide superior protection over the existing commercial vaccines.

2. Description of the Prior Art

There are three distinct serotypes of MD virus found in chickens: (1) serotype 1, the oncogenic form responsible for the disease, including high- and low-virulence MD virus and their attenuated variants; (2) serotype 2, a nononcogenic MD virus; and (3) serotype 3, herpesvirus of turkeys (HVT).

The prototype MD vaccine consists of the serotype 3 virus originally isolated from turkeys as reported in Witter et al. I [*Am. J. Vet. Res.* 31: 525–538 (1970)] and Okazaki et al., U.S. Pat. No. 3,642,574. Its lack of oncogenicity, self-limiting infection, good replication in vivo and in vitro, availability as cell-free and cell-associated preparations, and high protective efficacy have established HVT as a standard for MD vaccines throughout the world. A commonly used strain of HVT is FC126.

Vaccines produced from the naturally avirulent SB-1 strain [Schat et al., *J. Natl. Cancer Inst.* 60: 1075–1082 (1978) and U.S. Pat. No. 4,160,024], an isolate of a serotype 2 MD virus, have been licensed in the United States since 1984. The SB-1 strain is poorly protective against the highly virulent Md5 strain. It is usually used in combination with HVT as a bivalent vaccine since the two viruses together produce greater protection than does either one alone [Schat et al., *Avian Pathol.* 11: 593–606 (1982); Witter, *Avian Pathol.* 11: 49–62 (1982), herein incorporated by reference]. This phenomenon has been termed "protective synergism." The SB-1+HVT bivalent vaccine represents about 18% of the United States market for MD vaccines at present and is considered to be the most efficacious of the various MD products available. However, sporadic losses occur despite its use.

Another MD vaccine produced from strain CVI988 clone C (CVI988/C) has recently been licensed for commercial use in the United States. This vaccine is a mildly virulent serotype 1 MD virus attenuated by serial passage in tissue culture and has been reported by deBoer et al. [*Avian Dis.* 30: 276–283 (1986)].

An experimental vaccine derived from Md11, a very virulent serotype 1 MD field isolate, was reported by Witter, supra. Md11 was attenuated by 75 serial passages in cell culture, and the resultant vaccine designated Md11/75C. This vaccine has been shown to provide good protection against challenge with Md5 and most other highly virulent MD viruses tested; but it was less efficacious against challenge with the JM/102W strain, a prototype MD virus effectively protected against by HVT and SB-1 vaccines. Furthermore, its efficacy was consistently lower in chicks with HVT antibody.

In U.S. Pat. No. 4,895,717, Witter discloses a revertant derivative of Md11/75C which has been referred to as Md11/75C/R2. Md11/75C/R2 was shown to be superior to several other monovalent vaccines and was the equal of a bivalent (HVT+SB-1) vaccine [Witter, *Avian Dis.* 31: 752–765 (1987)]. However, the inherent pathogenicity of serotype 1 viruses and the potential of attenuated strains to revert to greater pathogenicity (Witter et al., *Avian Pathol.* 13: 75–92 (1984)] are factors to be considered in the licensing of such products.

Thus, although HVT, SB-1, CVI988/C, Md11/75C, and Md11/75C/R2 are all effective against certain MD viruses, none of these vaccines protect optimally against all MD challenge viruses in all chickens. In an effort to avert any large-scale outbreaks of MD in the future, the search for improved vaccines has continued.

An ideal serotype 1 vaccine probably should be derived from a very virulent MDV pathotype to optimize homology with the most pathogenic field strains likely to be encountered. It should be attenuated to the point of safety when applied to commercial chickens and either should be incapable of reversion or should not spread horizontally. It should replicate readily in vitro and in vivo. Finally, it should induce a high level of protection against early challenge with very virulent field strains in the presence of maternal antibodies against any of the viral serotypes.

SUMMARY OF THE INVENTION

I have now discovered two novel MD vaccines derived as clones of Md11/75C/R2. The clones are designated Md11/75/R2/23 and Md11/75/R2/29 and were selected from a pool of about 40 Md11/75C/R2 clones evaluated. The subject clones are uniquely characterized by a markedly reduced pathogenicity compared to the parent virus, without a comparable loss in immunogenicity. In experiments with a highly susceptible line of chickens, both clones failed to induce gross lesions of MD. Moreover, both clones induced immunity against challenge with very virulent strains of MDV that were nearly comparable to that of the parent virus. The observed level of immunity was not significantly different from the immunity provided by the bivalent (HVT+SB-1) vaccine.

In accordance with this discovery, it is an object of the invention to provide a novel, highly protective, serotype 1 vaccine against MD in chickens.

It is also an object of the invention to provide both monovalent and polyvalent vaccines against MD which are more efficacious than those presently in commercial use.

It is another object of the invention to improve the viability and productivity of chickens, particularly broilers and layers, and to reduce economic losses in the poultry industry caused by MD.

Another object of the invention is to provide an MD vaccine which is characterized by a rapid rate of replication, and thereby enhanced protective efficacy and in vitro production efficiency.

Other objects and advantages of this invention will become readily apparent from the ensuing description.

Deposit of Biological Material

Attenuated revertant serotype 1 Marek's disease virus clones Md11/75C/R2/23 and Md11/75C/R2/29 have been deposited under the provisions of the Budapest Treaty in the American Type Culture Collection, 10801 University Boulevard, Manassas, Va. 20110-2209, on May 22, 1991, and have been assigned Accession Nos. ATCC VR 2328 and ATCC VR 2327, respectively.

DETAILED DESCRIPTION OF THE INVENTION

"Vaccine" is defined herein in its broad sense to refer to any type of biological agent in an administratable form capable of stimulating an immune response in an animal inoculated with the vaccine. For purposes of this invention, the vaccine may comprise either the virus itself or an immunogenic (antigenic) component of the virus. The vaccine may also be produced from a vector having inserted therein a gene which encodes an immunogenic component of the virus.

The term "revertant" is intended to refer to a subculture of an attenuated virus, the subculture being characterized by increased virulence and increased in vivo replication as compared to the attenuated form. The term is used herein generically to encompass both true revertants and apparent revertants, the latter being derived from a population of viral particles rather than from a cloned virus.

As previously mentioned, the Md11/75C/R2/23 and Md11/75C/R2/29 clones are derived from the Md11/75C/R2 (R2) revertant virus of Witter (U.S. Pat. No. 4,895,717), supra. They were obtained by serially passing R2 in chicken embryo fibroblasts (CEF), and at passage 100 isolating cell-free virus. As with the R2, there appears to be a positive correlation between increase in replicative ability in vivo and increase in protectivity against challenge viruses. Thus, replicative rate may be used as an indicator of protectivity against challenge viruses.

As derivatives of the very virulent Md11 strain, both R2 clones should have good homology with other viruses of this pathotype. They are attenuated to the point where, except on rare occasion, no gross or histological lesions are induced even in genetically susceptible, maternal antibody negative chickens. Both reverted to greater virulence upon backpassage in chickens, but the danger associated with such reversion is minimized by the failure of either virus to spread to uninoculated chickens. The concern for pathogenicity of the clones is especially minimized for chickens protected either by maternal antibodies or by genetic resistance.

The viruses replicate well in vitro and induce readily detectable viremias in vivo. Both induce levels of protection against early challenge with very virulent MD viruses that exceed that of HVT alone and do not differ significantly from those of HVT+SB-1 bivalent or R2 vaccines.

A cell-associated vaccine can be prepared directly from in vitro culture cloning medium. To prepare cell-free virus inocula, cells from infected host tissue or cell culture are sonicated or otherwise disrupted. The cellular debris is removed by centrifugation and the centrifugate recovered as the inoculum. For a cell-free inoculum, the virus can be isolated as previously described. It is also an embodiment of the invention to prepare vaccines from the killed virus or from immunogenic components separated from the virus. For example, a subunit vaccine can be prepared by separating from the killed virus one or more purified viral proteins identified as having immunogenic properties.

It is envisioned within the ambit of the invention that the gene or genes encoding the immunogenic component or components responsible for the protective ability of the cloned viruses could be inserted into a suitable vector system by recombinant techniques as known in the art. The methodology involving recombinant DNA techniques has now become routine in science and has been successfully demonstrated in analogous applications [E. Paoletti et al., Proc. Natl. Acad. Sci. U.S.A. 81: 193–197 (1984)]. Specifically, the process would first involve the identification of proteins or other components of the clone that are critical to the induction of protective immunity. Next, specific regions of the viral genome (genes) along with an endogenous promoters would be identified and characterized through mapping with restriction endonucleases and determination of the nucleotide sequences. The identified gene or genes would then be spliced into expression vectors such as bacterial plasmids (to produce a killed protein product) or live viruses such as avian herpesviruses or avian poxviruses (to produce a live recombinant DNA vaccine virus). Other types of expression vectors could also be used. Once properly constructed with the necessary promoter sequences, the expression vector will produce the product of the inserted gene; namely, the critical immunizing protein or proteins of the clone. If produced by a vector grown in vitro, the immunizing protein will be obtained from the culture medium, purified, and used with appropriate adjuvants and diluents as a killed vaccine for the immunization of chickens. Other vectors, chosen for their natural infectivity for chickens, will be inoculated directly into chickens as a recombinant live virus vaccine. The vaccine will then produce the immunizing protein in vivo, thus causing protection directly and without the need for additional inoculations.

Thus, it is apparent from the above discussion that viral agents contemplated within the scope of the invention originating from the R2/23 and R2/29 clones include both cell-free and cell-associated virus and also live and killed virus. Also contemplated as the viral agent are antigens which are effective to elicit an immune response in chickens to Marek's disease virus, whether those antigens have been derived directly from the R2/23 or R2/29 clones, or expressed by a recombinant virus as described, supra.

The viral agent is prepared for administration by formulation in an effective immunization dosage with a pharmaceutically acceptable carrier or diluent, such as physiological saline or tissue culture medium. The expression "effective immunization dosage" is defined as being that amount which will induce immunity in a chicken against challenge by a virulent strain of MD. Immunity is considered as having been induced in a population of chickens when the level of protection for the population is significantly higher than that of an unvaccinated control group. One measure of the level of protection is the protective index (PI), which is calculated as the MD in unvaccinated, MD virus challenged controls minus the MD in vaccinated, MD virus challenged groups, and the difference divided by the percent MD in unvaccinated, MD virus challenged controls, with the result multiplied by 100. Typically, the vaccine will contain at least about 1500 PFU (plaque-forming units) of the virus, and preferably between 2000 and 5000 PFU. The vaccine can be effectively administered anytime after the chicken attains immunocompetence, which is at about the 18th day of incubation (3 days prehatch); but it is normally administered by inoculation within 24–48 hrs after hatching.

Appropriate adjuvants as known in the art may also be included in the vaccine formulation. In many cases, the vaccinal efficacy can be enhanced by combining the R2/23 or R2/29 with other viral agents into bivalent or polyvalent vaccines.

The following examples are intended only to further illustrate the invention and are not intended to limit the scope of the invention which is defined by the claims.

EXAMPLE 1

Two clones useful as vaccines in accordance with this invention were produced from Md11/75C/R2 (designated hereafter as R2) by serially passing the R2 revertant in CEF. At passage 100, cell-free virus was isolated from sonicated, heavily-infected CEF culture and used to initiate 30 clones, each of which was grown into stocks for evaluation at passage 101. These clones were designated R2/1–R2/30.

EXAMPLE 2

The 30 clones obtained in Example 1 were split into groups and each evaluated in one of six trials for inducement of viremia, gross lesions and histological lesions in chickens. The chickens used for this experiment were $F_1$ progeny (15×7) of Regional Poultry Laboratory line $15I5_5$ males and line $7_1$ females. The parent females were unvaccinated breeder hens that were free of antibodies to MD virus and HVT and the progeny chickens were considered negative for maternal antibodies (ab–). The chickens were inoculated intraabdominally with 20,000 PFU of virus at 1 day of age. After being held in isolators for 8 wks, they were killed and examined for gross lesions. Blood samples were obtained for measuring viremia, and tissues were examined for histological lesions. Controls for each trial included two lots inoculated with R2 (used at the 87th passage), one lot inoculated with Md5, and one uninoculated lot. The Md5 virus stock was a suspension of infected tissue-culture cells cryopreserved with 10% dimethylsulfoxide at –196° C. The results of the evaluations are given in Table I below. Nine preparations induced detectable viremia in the absence of gross MD lesions, characteristics considered desirable for candidate vaccine viruses. The absence of gross lesions was considered significant because the parent R2 virus induced gross lesions in one or more chickens in each of 12 replicate trials.

EXAMPLE 3

Clones R2/13, R2/22, R2/23, and R2/29 were selected for further evaluation as candidate vaccine viruses. Chickens (15×7 ab–) as described in Example 1 were inoculated intraabdominally with 20,000 PFU virus at 1 day of age. After being held in isolators for 2, 4, 8, or 18 wks, the chickens were killed and examined for viremia, gross lesions, and histological lesions as in Example 2. The reported viremia values are mean PFU counts of two white blood cell (WBC) pools (three birds each), $10^6$ buffy coat cells/culture. For each treatment, body weights were determined as the means of all survivor birds at 17 wks, adjusted for sex. The results are reported in Table II.

In contrast to the trial in Example 1, clones R2/13 and R2/22 produced gross and histological lesions at frequencies similar to that of the R2 parent virus. However, clone R2/23 induced no gross or microscopic lesions. Clone R2/29 also appeared relatively apathogenic although one chicken died at 17 wks, apparently with gross MD lesions. This chicken was not examined histologically and may have been misdiagnosed, considering the absence of gross or histological lesions in cagemates killed at 18 wks. Both R2/23 and R2/29 induced viremias, but at lower titers than R2 or the other clones. Body weights of the groups did not differ from that of the uninoculated controls.

Clones R2/23 and R2/29 were deposited under the Budapest Treaty, in the American Type Culture Collection, 10801 University Boulevard, Manassas, Va. 20110-2209, on May 22, 1991, assigned Accession Nos. ATCC VR 2328 and ATCC VR 2327, respectively.

Data were analyzed by Bonferroni's modification of Student's t-test, in which the value of t for two groups was based on a variance computed from all groups, and the values of t required for statistical significance were adjusted for the number of paired observations made.

EXAMPLE 4

A series of experiments were conducted to evaluate the ability of R2/23 and R2/29 to immunize chickens against challenge with virulent MD viruses. The chickens were 15×7 as used in Example 2 except they were obtained from breeder hens vaccinated with all three MD serotypes, i.e., Md11/75C (serotype 1), SB-1 (serotype 2), and FC126 (serotype 3) at a dose of 1000 PFU for each virus and were considered positive for maternal antibodies (ab+). In the first experiment, each chicken was inoculated at 1 day of age with 2000 PFU of R2, R2/23, R2/29, FC126/2, or FC126/2+SB-1 (2000 PFU of each) and placed in a modified Horsfall-Bauer isolator. The FC126/2 is a clone of FC126. At 5 days post vaccination, each chicken was challenged with 500 PFU of Md5 virus. The birds were held for about 56 days post challenge, killed and necropsied, and the presence of gross lesions was recorded. Birds dying during the experiment were examined for gross lesions. The birds considered to be at risk were those positive for MD lesions plus those survivors without lesions. The percent protection was calculated as the percent MD in unvaccinated, challenged controls minus the percent MD in vaccinated, challenged groups divided by the percent MD in unvaccinated, challenged controls multiplied by 100.

Three replicate treats were run, and the pooled results are reported in Table III below. Both the R2/23 and R2/29 clones provided protection that was greater than that of HVT (FC126/2) alone, and was not statistically different from that of R2 or HVT+SB-1 vaccines.

EXAMPLE 5

A second challenge experiment was conducted substantially as described in Example 4, except serotype 1 challenge viruses RB1B, 295, and 287L were substituted for Md5. The results are reported in Table IV below.

EXAMPLE 6

A third challenge experiment was conducted substantially as described in Example 4, except protection was evaluated in various chicken strains. The strains used were 15×7 ab+ and two commercial White Leghorn stocks, WL-A, and WL-B. Both WL-A and WL-B were from parents that received serotype 2 and 3 MD vaccines and, consequently, were considered positive for maternal antibodies. The results are reported in Table V below.

EXAMPLE 7

Clones R2/23 and R2/29 were evaluated to determine if protection was diminished by additional passage of the virus stocks in cell culture. The procedure of Example 4 was repeated, except the clones were carried through to either passage 105 or passage 115. The results are reported in Table VI below.

EXAMPLE 8

The R2 clones, plus low passage Md11 as a positive control, were backpassaged in ab− chickens as described in Example 2 to monitor the ability of the viruses to revert to greater virulence. The inocula for passages 2, 3, and 4 were derived from an inoculated chicken in the previous passage. In addition, each group contained contact control chickens to monitor the ability of the viruses to spread by a natural route.

Viremia was determined from buffy-coat cells from one 0.2-ml sample of blood pooled from two representative chickens. The blood was collected at 2 wks in each backpassage. Assays were conducted in triplicate by standard procedures on chicken or duck embryo fibroblast cultures. Antibodies were detected in sera of test chickens by an indirect immunofluorescence test using antigen consisting of cells infected with R2 virus.

The results of backpassaging are shown in Table VII. Pathogenicity and viremia titers of both R2 clones increased with backpassage; most of the increase occurred between the first and second backpassages. Based on the frequency of gross MD lesions in chickens inoculated in backpassages 2–4, the virulence of clone backpassaged R2/29 (16/36 positive) appeared greater than the virulence of backpassaged clone R2/23 (6/36 positive) (P<0.05). Importantly, neither R2 clone was spread horizontally as indicated by the lack of gross lesions or antibodies through 8 wks in contact control chickens at any backpassage.

EXAMPLE 9

A trial was conducted to test whether additional in vitro passages would change the avirulent nature of the R2 clones. Ab+ chickens were inoculated and challenged as described in Example 4. No differences between passages 105 and 115 were observed for either virus in gross or histologic lesions, body weights, or viremias. Both viruses were less pathogenic and induced lower viremia titers than the parent R2 virus. Curiously, body weights were higher in virus-inoculated chickens than in uninoculated controls. The results are reported in Table VIII below.

EXAMPLE 10

The growth rate of R2, R2/23, and FC126/2 in chicken embryo fibroblast cultures was compared. Cultures were inoculated with about 100 PFU of each virus, and six replicate cultures per virus were assayed for cell-associated infectivity on days 1, 3, 5, 7, and 9. The results were expressed as a ratio of PFU to the input PFU, as determined by titration of the original inoculum. on day 7, an additional 6 replicate cultures per virus were assayed for cell-free infectivity. For cell-free virus assay, the designated plates were trypsinized and the cell harvest was resuspended in 1.0 ml of SPGA buffer, treated in two cycles (15 sec and 5 sec) with a sonifier (Heat Systems Ultrasonic, Farmingdale, N.Y.) at a power setting of 2 and a wattage setting of 40, and centrifuged at 6000×g for 10 min. The supernate was removed and assayed by inoculation of drained cultures with 0.1 ml. Medium was replenished after absorption for 30 min.

The comparative rates of in vitro replication of R2/23, R2, and FC126/2 are given in Table IX. Titers (PFU/input PFU) of R2/23 were somewhat lower than that of R2 on days 1, 3, and 5 (P<0.05), but did not differ from R2 on days 7 and 9. Neither serotype 1 virus at any time replicated to as high a titer as did FC126/2. However, it is likely that differences in PFU per input PFU may reflect differences in infection efficiency than in rate of replication. Cell-free virus recovery by sonication of infected cultures 7 days post inoculation was negligible for both serotype 1 viruses and was considerably less cored to that of FC126/2 (P<0.05).

EXAMPLE 11

CEF cultures in 96-well plates were infected with selected MD viruses of serotypes 1, 2, and 3 and fixed in cold acetone-alcohol when plaques became apparent. The cultures were stained by indirect immunofluorescence with serial dilutions of serotype specific monoclonal antibodies H19 and 2BN90 (serotype 1), Y5 (serotype 2), and L78 (serotype 3). Titers were the highest dilution of antibody that produced a positive reaction on the infected cell antigen.

Antigenic analysis by serotype-specific monoclonal antibodies as reported in Table X showed that R2/23, R2/29, and the parent R2 virus gave similar results; each reacted strongly with serotype 1-specific antibodies H19 and 2BN90 but not with antibodies of other serotypes. In accord with other reports in the literature, CVI988/Rispens and CVI988/C both lacked reactivity with H19 antibody but could be classified as serotype 1 strains by their reactivity with 2BN90. Control antibodies Y5 and L78 stained only serotype 2 and 3 antigens, respectively.

It is understood that the foregoing detailed description is given merely by way of illustration and that modification and variations may be made therein without departing from the spirit and scope of the invention.

TABLE I

Evaluation of R2 Derivative Clones in Ab- Chickens

| | | Viremia | | Gross lesions | Histo lesions |
|---|---|---|---|---|---|
| Clone | Passage | +/Tot | Mean PFU | +/tot | +/tot |
| Random clones | | | | | |
| R2/1 | 101 | 0/5 | 0.0 | 0/12 | 0/12 |
| R2/2 | 101 | 0/4 | 0.0 | 3/11 | ND |
| R2/3 | 101 | 0/4 | 0.0 | 0/11 | 0/11 |
| R2/4 | 101 | 0/3 | 0.0 | 3/11 | ND |
| R2/5 | 101 | 2/4 | 1.2 | 3/12 | ND |
| R2/6[c] | 101 | 2/5 | 3.2 | 0/11 | 4/11 |
| R2/7 | 101 | 0/4 | 0.0 | 0/12 | ND |
| R2/8 | 101 | 0/5 | 0.0 | 0/12 | ND |
| R2/9 | 101 | 6/6 | 6.0 | 1/12 | ND |
| R2/10 | 101 | 6/6 | 16.3 | 1/11 | 3/12 |
| R2/11 | 101 | 6/6 | 8.2 | 1/11 | ND |
| R2/12 | 101 | 6/6 | 19.0 | 3/12 | ND |
| R2/13[cd] | 101 | 5/6 | 12.0 | 0/9 | 3/9 |
| R2/14 | 101 | 6/6 | 26.8 | 1/12 | ND |
| R2/15 | 101 | 4/6 | 4.2 | 1/12 | ND |
| R2/16 | 101 | 6/6 | 8.0 | 1/11 | 2/11 |
| R2/17 | 101 | 6/6 | 56.2 | 6/11 | ND |
| R2/18 | 101 | 6/6 | 9.3 | 2/12 | 6/12 |
| R2/19 | 101 | 6/6 | 6.0 | 1/12 | ND |
| R2/20 | 101 | 5/6 | 33.3 | 1/12 | ND |
| R2/21[c] | 101 | 1/6 | 0.3 | 0/12 | ND |
| R2/22[cd] | 101 | 6/6 | 10.8 | 0/10 | 2/10 |
| R2/23[cd] | 101 | 4/6 | 2.0 | 0/11 | 1/11 |
| R2/24 | 101 | 6/6 | 45.7 | 2/12 | ND |
| R2/25 | 101 | 4/6 | 10.3 | 1/12 | 1/12 |
| R2/26 | 101 | 4/5 | 15.5 | 1/12 | ND |
| R2/27[c] | 101 | 3/6 | 2.0 | 0/12 | 0/12 |
| R2/28[c] | 101 | 3/6 | 0.8 | 0/11 | 1/11 |
| R2/29[cd] | 101 | 4/6 | 0.7 | 0/12 | 0/12 |
| R2/30[c] | 101 | 1/6 | 0.2 | 0/11 | ND |
| Control R2 | | | | | |
| R2 | 88 | 5/6 | 9.5 | 4/12 | 7/12 |
| R2 | 88 | 3/6 | 19.3 | 4/11 | 5/11 |
| R2 | 88 | 4/6 | 4.8 | 1/12 | 4/12 |
| R2 | 88 | 5/6 | 9.7 | 1/11 | 7/11 |
| R2 | 88 | 6/6 | 21.8 | 3/12 | 4/12 |
| R2 | 88 | 4/6 | 33.7 | 3/11 | 7/11 |
| R2 | 88 | 6/6 | 118.0 | 2/12 | 8/12 |
| R2 | 88 | 6/6 | 41.2 | 5/12 | 9/12 |
| R2 | 89 | 5/6 | 38.2 | 2/11 | 4/11 |
| R2 | 89 | 6/6 | 8.3 | 3/11 | 5/11 |
| R2 | 89 | 6/6 | 10.7 | 1/12 | 8/12 |
| R2 | 89 | 6/6 | 11.2 | 3/12 | 7/12 |

TABLE I-continued Evaluation of R2 Derivative Clones in Ab- Chickens

| Clone | Passage | Viremia +/Tot | Mean PFU | Gross lesions +/tot | Histo lesions +/tot |
|---|---|---|---|---|---|
| Control Md5 | | | | | |
| Md5 | 7 | ND | ND | 10/11 | ND |
| Md5 | 7 | ND | ND | 12/12 | ND |
| Md5 | 7 | ND | ND | 11/11 | ND |
| Md5 | 7 | ND | ND | 10/10 | ND |
| Md5 | 7 | ND | ND | 12/12 | ND |
| Md5 | 7 | ND | ND | 12/12 | ND |
| Uninoculated Controls | | | | | |
| . . . | | ND | ND | 0/11 | 0/11 |
| . . . | | ND | ND | 0/12 | 0/12 |
| . . . | | ND | ND | 0/12 | 0/12 |
| . . . | | ND | ND | 0/10 | 0/10 |
| . . . | | ND | ND | 0/10 | 0/10 |
| . . . | | ND | ND | 0/12 | 0/12 |

[a]Chickens negative for materal antibodies inoculated with 20,000 PFU of virus at 1 day of age. Obsesvations made 8 wks post inoculation. A series of six trials was conducted; controls for each trial included two lots inoculated with R2, one lot inoculated with Md5 and one uninoculated lot.
[b]ND = not done.
[c]Clones inducing viremia in absence of gross lesions.
[d]Clones selected for further study.

TABLE II

Pathogenicity of Four R2 Clones[a]

| Clone | Wks | Gross lesions +/tot | % | Histo lesions +/tot | % | Viremia PFU[b] | Adjusted body wt. g[c] |
|---|---|---|---|---|---|---|---|
| R2 | 2 | 0/3 | 0 | 1/3 | 33 | 218.5 | |
| | 4 | 0/4 | 0 | 0/4 | 0 | 19.8 | |
| | 8 | 1/8 | 13 | 5/5 | 100 | 77.8 | |
| | 18 | 10/25 | 40 | 2/6 | 33 | 12.8 | 1502 a |
| R2/13 | 2 | 6/4 | 0 | 0/4 | 0 | 137.3 | |
| | 4 | 0/4 | 0 | 1/4 | 25 | 36.0 | |
| | 8 | 1/9 | 11 | 3/6 | 50 | 69.0 | |
| | 18 | 6/24 | 25 | 2/6 | 33 | 39.5 | 1449 ab |
| R2/22 | 2 | 0/6 | 0 | 0/6 | 0 | 127.0 | |
| | 4 | 0/6 | 0 | 2/6 | 33 | 29.5 | |
| | 8 | 1/7 | 14 | 2/3 | 67 | 76.0 | |
| | 18 | 8/22 | 36 | 4/6 | 67 | 64.5 | 1559 a |
| R2/23 | 2 | 0/6 | 0 | 0/6 | 0 | 19.3 | |
| | 4 | 0/5 | 0 | 0/5 | 0 | 1.0 | |
| | 8 | 0/9 | 0 | 0/6 | 0 | 6.3 | |
| | 18 | 0/21 | 0 | 0/6 | 0 | 2.0 | 1593 ac |
| R2/29 | 2 | 0/5 | 0 | 0/5 | 0 | 31.0 | |
| | 4 | 0/6 | 0 | 0/6 | 0 | 8.3 | |
| | 8 | 0/9 | 0 | 0/6 | 0 | 5.0 | |
| | 18 | 1/22[d] | 5 | 0/6 | 0 | 6.3 | 1593 ac |
| None | 2 | 0/5 | 0 | 0/5 | 0 | 0.0 | |
| | 4 | 0/6 | 0 | 0/6 | 0 | 0.0 | |
| | 8 | 0/6 | 0 | 0/6 | 0 | 0.0 | |
| | 18 | 0/22 | 0 | 0/6 | 0 | 0.0 | 1534 a |

[a]Chickens negative for maternal antibodies inoculated at 1 day of age with 20,000 PFU of each virus.
[b]Viremias are mean PFU counts of two WBC pools (three birds each), $10^6$ buffy coat cells/culture.
[c]Body weights are means of all survivor birds at 17 wks, adjusted for sex. Means with different letter designations differ by Bonferroni t-test ($P < 0.05$).
[d]Bird died at 17 wks with enlarged vagus, sciatic, and brachial nerves. No histology was done.

TABLE III

Comparative Efficacy of Vaccines from Attenuated R2 Clones[a]

| Trial vaccine | MD Response +/Tot | % MD | % Protection | Survivor weights N | g |
|---|---|---|---|---|---|
| R2 | 11/50 | 22.0 | 78 b[b] | 48 | 700.3 b |
| R2/23 | 16/51 | 31.4 | 69 b | 49 | 708.2 b |
| R2/29 | 17/51 | 33.3 | 67 b | 49 | 705.1 b |
| FC126/2 | 39/51 | 76.5 | 24 a | 50 | 707.6 b |
| FC126/2 + SB1 | 11/50 | 22.0 | 78 b | 49 | 716.8 b |
| None | 51/51 | 100.0 | | 45 | 523.8 a |
| None (no chall) | 0/15 | 0.0 | | 15 | 759.6 b |

[a]Chickens positive for materal antibodies were inoculated at 1 day of age with 2000 PFU of each virus, challenged with 500 PFU of Md5 virus at 5 days post vaccination, and evaluated at 8 wks post challenge.
[b]Statistics by Chi-Sguare (protection), Bonferroni t-test (weights). Values with different letter designations differ ($P < 0.05$).

TABLE IV

Protection by R2 Clones Against Different Challenge Viruses[a]

| Vaccine | Challenge | +/Tot | % MD | % Protection |
|---|---|---|---|---|
| R2/23 | RB1B | 8/17 | 47.1 | 50 a[b] |
| R2/29 | | 6/17 | 35.3 | 63 a |
| FC126/2 | | 8/17 | 47.1 | 50 a |
| FC126/2 + SB-1 | | 0/17 | 0.0 | 100 b |
| None | | 16/17 | 94.1 | |
| R2/23 | 295 | 8/17 | 47.1 | 38 a |
| R2/29 | | 11/16 | 68.8 | 10 a |
| FC126/2 | | 11/17 | 64.7 | 15 a |
| FC126/2 + SB-1 | | 10/17 | 58.8 | 23 a |
| None | | 13/17 | 76.5 | |
| R2/23 | 287L | 6/17 | 35.3 | 62 a |
| R2/29 | | 4/17 | 23.5 | 75 a |
| FC126/2 | | 9/17 | 52.9 | 44 a |
| FC126/2 + SB-1 | | 9/17 | 52.9 | 44 a |
| None | | 15/16 | 93.8 | |
| R2/23 | total | 22/51 | 43.1 | 51 a |
| R2/29 | | 21/50 | 42.0 | 52 a |
| FC126/2 | | 38/51 | 54.9 | 38 a |
| FC126/2 + SB-1 | | 19/51 | 37.3 | 58 a |
| None | | 44/50 | 88.0 | |

[a]Chickens positive for maternal antibodies were inoculated at 1 day of age with 2000 PFU of each virus, challenged with 500 PFU of the appropriate virus at 5 days post vaccination, and evaluated at 8 wks post challenge.
[b]Statistics by Chi-Sguare. Values witn different letter designations differ ($P < 0.05$).

TABLE V

Protection by R2 Clones Against MD in Different Chicken Strains[a]

| Vaccine | Chicken | +/Tot | % MD | % Protection |
|---|---|---|---|---|
| R2/23 | 15 × 7 ab+ | 4/17 | 23.5 | 76 b[b] |
| R2/29 | | 8/17 | 47.1 | 53 ab |
| FC126 | | 13/17 | 76.5 | 24 a |
| FC126 + SB-1 | | 3/16 | 18.8 | 81 b |
| None | | 17/17 | 100.0 | |
| R2/23 | WL-A | 0/16 | 0.0 | 100 a |
| R2/29 | | 1/17 | 5.9 | 94 a |
| FC126 | | 4/17 | 23.5 | 75 a |
| FC126 + SB-1 | | 1/16 | 6.3 | 93 a |
| None | | 14/15 | 93.3 | |
| R2/23 | WL-B | 2/16 | 12.5 | 82 a |
| R2/29 | | 1/16 | 6.3 | 91 a |
| FC126 | | 3/17 | 17.6 | 75 a |

TABLE V-continued

Protection by R2 Clones Against MD in Different Chicken Strains[a]

| Vaccine | Chicken | +/Tot | % MD | % Protection |
|---|---|---|---|---|
| FC126 + SB-1 | | 0/17 | 0.0 | 100 a |
| None | | 12/17 | 70.6 | |
| Pooled data: | | | | |
| R2/23 | | 6/49 | 12.2 | 86 b |
| R2/29 | | 10/50 | 20.0 | 77 ab |
| FC126/2 | | 20/51 | 39.2 | 55 a |
| FC126/2 + SB-1 | | 4/49 | 8.2 | 91 b |
| None | | 43/49 | 87.8 | |

[a]Chickens positive for maternal antibodies were inoculated at 1 day of age with 2000 PFU of each virus, challenged with 500 PFU of Md5 virus at 5 days post vaccination, and evaluated at 9 wks post challenge.
[b]Statistics by Chi-Square. Values with different letter designations differ ($P < 0.05$).

TABLE VI

Effect of Additional Cell Culture Passage on Protection[a]

| Vaccine | Passage | +/Tot | % POS | % Protection |
|---|---|---|---|---|
| R2/23 | 105 | 16/34 | 47.1 | 53 a[b] |
| R2/23 | 115 | 12/34 | 35.5 | 65 a |
| R2/29 | 105 | 12/32 | 37.5 | 63 a |
| R2/29 | 115 | 17/34 | 50.0 | 50 a |
| None | | 34/34 | 100.0 | |

[a]Chickens positive for maternal antibodies were inoculated at 1 day of age with 2000 PFU of each virus, challenged with 500 PFU of Md5 virus at 5 days post vaccination, and evaluated at 8 wks post challenge. Data pooled from two replicate trials.
[b]Statistics by Chi-Square. Values with different letter designations differ ($P < 0.05$).

TABLE VII

Backpassage of R2 Clones

| | | Inoculates | | | Contacts | | |
|---|---|---|---|---|---|---|---|
| Virus | Back-passage | Viremia[a] | Antibody[b] | Gross lesions[c] | Viremia | Antibody | Gross lesions |
| R2/23 | 1 | 0 | 6/7 | 0/7 | 0 | 0/7 | 0/6 |
| | 2 | 150 | 8/12 | 3/12 (0) | 0 | 0/10 | 0/12 |
| | 3 | 67 | 12/12 | 1/12 | 0 | 0/12 | 0/12 |
| | 4 | 57 | 12/12 | 2/12 (0) | 0 | 0/11 | 0/11 |
| R2/29 | 1 | 3 | 6/7 | 0/7 | 0 | 0/6 | 0/6 |
| | 2 | 375 | 11/12 | 4/12 (0) | 0 | 0/11 | 0/11 |
| | 3 | 46 | 8/12 | 4/12 (0) | 0 | 0/12 | 0/12 |
| | 4 | 98 | 12/12 | 8/12 (0) | 0 | 0/12 | 0/12 |
| Md11 | 1 | 8 | 1/1 | 6/6 (6) | 0 | 4/6 | 6/6 (0) |
| | 2 | 213 | 0/1 | 11/11 (11) | 0 | 8/11 | 12/12 (0) |
| | 3 | 380 | ND | 12/12 (12) | 0 | 8/11 | 10/11 (0) |
| | 4 | 382 | ND | 11/11 (11) | 0 | 8/11 | 10/12 (1) |
| Control | 1 | 0 | 0/4 | 0/5 | | | |
| | 2 | 0 | 0/12 | 0/12 | | | |
| | 3 | 0 | 0/11 | 0/12 | | | |
| | 4 | 0 | 0/12 | 0/12 | | | |

[a]PFU from $10^6$ buffy coat cells from one sample of blood pooled from two representative chickens and assayed in triplicate. Blood collected at 2 wks (backpasage 1–4).
[b]Antibody detected by indirect immunofluorescence on antigen consisting of cells infected with R2 virus. Sera collected at 8 wks. Number positive/number tested.
[c]Gross MD lesions at 8 wks. Number positive/number examined. Number dead in parentheses.

TABLE VIII

Effect of Additional Tissue Culture Passage on Pathogenicity and Replication of R2 Clones[a]

| Virus | Passage | Gross Lesions +/tot | Gross Lesions % | Histo Lesions +/tot | Histo Lesions % | Body Wt. g | Viremia PFU |
|---|---|---|---|---|---|---|---|
| R2/23 | 105 | 0/10 | 0.0 | 0/10 | 0.0 | 580.5 b[b] | 1.4b |
| R2/23 | 115 | 0/10 | 0.0 | 0/10 | 0.0 | 569.7 b | 11.1b |
| R2/29 | 105 | 0/10 | 0.0 | 0/10 | 0.0 | 604.7 b | 17.5b |
| R2/29 | 115 | 0/8 | 0.0 | 0/8 | 0.0 | 549.3 b | 8.9b |
| R2 | 89 | 3/10 | 30.0 | 6/10 | 60.0 | 685.0 c | 180.7c |
| None | | 0/10 | 0.0 | 0/10 | 0.0 | 521.5 a | 0.0a |

[a]Chickens positive for maternal antibodies were inoculated at 1 day of age with 2000 PFU of each virus, challenged with 500 PFU of Md5 virus at 5 days post vaccination, and evaluated at 8 wks post challenge.
[b]Statistics by Bonferroni t-test. Values with different letter designations differ ($P < 0.05$).

TABLE IX

Replication of R2 Clones

| | Cell-associated | | | | | Cell-free |
|---|---|---|---|---|---|---|
| Virus | Day 1 | Day 3 | Day 5 | Day 7 | Day 9 | day 7 |
| R2/23 | 3.5a[a] | 82.1a | 296.7a | 718.0a | 1052.8a | 1.4a |
| R2 | 8.0b | 163.2b | 588.2b | 833.4a | 1481.5a | 1.4a |
| FC126/2 | 13.6c | 237.3c | 1119.3c | 1323.5b | 1905.6b | 100.5b |

[a]Values for same day followed by different letter are different ($P < 0.05$) by Bonferroni t-test. Values are means of six replicates and are expressed as PFU per input PFU.

TABLE X

Antigenic Analysis of R2 Clones by Monoclonal Antibodies

| Virus | Monoclonal antibody | | | |
|---|---|---|---|---|
|  | H19 | 2BN90 | Y5 | L78 |
| R2 | 102400[a] | 25600 | <50 | <50 |
| R2/23 | 51200 | 25600 | <50 | <50 |
| R2/29 | 51200 | 25600 | <50 | <50 |
| CVI988/Rispens | <50 | 12800 | <50 | <50 |
| CVI988/C | <50 | 12800 | <50 | <50 |
| SB-1 | <50 | <50 | 12800 | <50 |
| FC126/2 | <50 | <50 | <50 | 25600 |

[a]Titers are reciprocal of highest dilution of antibody reacting with viral antigen in indirect immunofluorescence assay.

I claim:

1. A vaccine comprising: (1) a live attenuated revertant virus clone having all of the identifying characteristics of Md11/75C/R2/23 or Md11/75C/R2/29 in a dosage effective to elicit an immune response to a Marek's disease virus and (2) a pharmaceutically acceptable carrier or diluent.

2. A vaccine as described in claim 1 wherein said viral clone is in a cell-associated preparation.

3. A vaccine as described in claim 1 wherein said viral clone is an attenuated revertant virus clone having all of the identifying characteristics of Md11/75C/R2/23.

4. A method for protecting a chicken against Marek's diseases comprising inoculating said chicken with a virus clone in a pharmaceutically acceptable carrier or diluent, wherein said virus clone is a live attenuated revertant virus clone having all of the identifying characteristics of Md11/75C/R2/23 or Md11/75C/R2/29 in a dosage effective to elicit an immune response to a Marek'disease virus.

5. A method as described in claim 4 wherein said virus clone is in a cell-associated preparation.

6. A method as described in claim 4 wherein said virus clone is an attenuated revertant virus clone having all of the identifying characteristics of Md11/75C/R2/23.

* * * * *